United States Patent
Ring et al.

(10) Patent No.: US 7,473,709 B2
(45) Date of Patent: Jan. 6, 2009

(54) 11β-BENZALDOXIME DERIVATIVES OF D-HOMOOESTRA-4,9-DIEN-3-ONES

(75) Inventors: Sven Ring, Jena (DE); Gerd Schubert, Jena (DE); Lothar Sobek, Jena (DE)

(73) Assignee: Bayer Schering Pharma AG, Berlin (DE)

( * ) Notice: Subject to any disclaimer, the term of this patent is extended or adjusted under 35 U.S.C. 154(b) by 67 days.

(21) Appl. No.: 11/635,076

(22) Filed: Dec. 7, 2006

(65) Prior Publication Data

US 2007/0149621 A1     Jun. 28, 2007

(30) Foreign Application Priority Data

Dec. 8, 2005   (DE) ................ 10 2005 059 222

(51) Int. Cl.
  *A61K 31/15*   (2006.01)
  *C07C 251/32*  (2006.01)
(52) U.S. Cl. ..................... 514/640; 564/253
(58) Field of Classification Search ............ 564/253; 514/640
  See application file for complete search history.

(56) References Cited

U.S. PATENT DOCUMENTS

| | | | |
|---|---|---|---|
| 4,536,401 A | 8/1985 | Neef et al. | |
| 5,519,027 A | 5/1996 | Schwede et al. | |
| 5,576,310 A | 11/1996 | Schubert et al. | |
| 5,693,628 A | 12/1997 | Schubert et al. | |
| 6,365,582 B1 | 4/2002 | Schubert et al. | |

OTHER PUBLICATIONS

Elger W et al, Endocrine pharmacological characterization of progesterone antagonists and progesterone receptor modulators with respect to PR-agonistic and antagonistic activity, Oct. 2000, pp. 713-723, Steroids, Butterworth-Heinemann, Stoneham, MA, US.

*Primary Examiner*—Barbara P Badio
(74) *Attorney, Agent, or Firm*—Millen, White, Zelano & Branigan, P.C.

(57) ABSTRACT

The present patent application relates to 11β-benzaldoxime derivatives of D-homooestra-4,9-dien-3-ones of formula I:

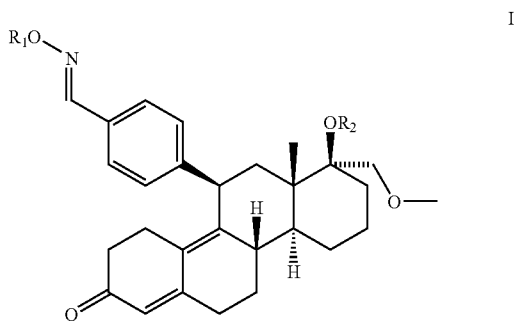

wherein
$R_1$ is a hydrogen atom or a $C_1$-$C_6$-alkyl, $C_1$-$C_6$-acyl, $C_1$-$C_4$-alkoxycarbonyl, $C_1$-$C_4$-alkylthiocarbonyl, $C_1$-$C_6$-alkylaminocarbonyl or arylaminocarbonyl group; and
$R_2$ is a hydrogen atom or a $C_1$-$C_6$-alkyl or $C_1$-$C_6$-acyl group.

Compounds of formula I bind more strongly to the glucocorticoid receptor than to the progesterone receptor and are effective antiglucocorticoids. According to the invention, they are suitable for the treatment and/or prevention of symptoms and/or diseases that are attributable to an androgen deficiency induced by glucocorticoids, especially cortisol.

7 Claims, No Drawings

11β-BENZALDOXIME DERIVATIVES OF D-HOMOOESTRA-4,9-DIEN-3-ONES

The present patent application relates to 11β-benzaldoxime derivatives of D-homooestra -4,9-dien-3-ones, to processes for their preparation, to pharmaceutical compositions containing the compounds according to the invention, and to their use for the treatment of the age-related and/or stress-related drop in the human testosterone level due to corticoids.

With advancing age and under physical and/or mental stress in the human organism, the corticoid level increases relative to the sex hormone level and can therefore lead to sexual dysfunctions and hypogonadism in men (EP 1285927). These diseases are due to a reduced endogenous production of androgens, especially a reduced production of testosterone in the testes, and to the age-related excess of corticoids, which causes a more rapid and increased breakdown of endogenous testosterone.

Glucocorticoid receptor antagonists are compounds that competitively inhibit the action of glucocorticoids by binding more strongly and more selectively to the glucocorticoid receptors.

WO 95/04536 describes the application of glucocorticoid receptor antagonists for the treatment of anxiety disorders. Furthermore, a number of 11,21-bisphenyl-19-norpregnanes for the treatment of specific glucocorticoid-related diseases, such as Cushing's syndrome, diabetes, glaucoma, depression, arteriosclerosis, adiposis, high blood pressure, sleep disorders and osteoporosis, are described in EP 0683172, EP 0793541 and Bioorganic & Medicinal Chemistry Letters 1997, 7, 2229-2234. WO 01/47859 describes non-steroidal compounds as selective glucocorticoid receptor antagonists for the treatment of diabetes. Also, the antiglucocorticoid ORG 34 517 has been investigated in clinical studies for the indication of depression [Pharma Business 2002, 51, 152]. DE 10140113 lists compounds which have been investigated as antiglucocorticoids for the treatment of glucocorticoid-related hypogonadism.

EP 0057115 describes RU 38486 (mifepristone) as a glucocorticoid receptor antagonist that binds almost equally strongly to the progesterone and glucocorticoid receptors and is currently approved as a progesterone receptor antagonist for terminating a pregnancy in the early phase [M. Moguilewsky, D. Philibert, E. E. Baulieu; S. J. Segal, (Eds): The antiprogestin steroid RU 38486 and human fertility control, p. 87, Plenum Press, New York, London 1985] and is used as a glucocorticoid receptor antagonist for the treatment of Cushing's syndrome [L. K. Nieman, G. P. Chrousos, C. K. Kellner, I. M. Spitz, B. C. Nisula, J. Clin. Endocrin. Metab. 1985, 61, 536].

However, due to the lack of receptor selectivity, RU 38486 appears to be unsuitable for the long-term treatment of sexual dysfunctions and hypogonadism in men because of the side effects attributable to the antiprogestin activity.

11β-Aryl-substituted D-homooestra-4,9-dienes are disclosed in DE 3320580 and EP 414606. As antigestagens they are superior to the compound RU 38486 in terms of abortive action. D-homo-(16)en-11β-aryloestrenes are known from DE 4042005. They possess potent antigestagen, antiglucocorticoid, antimineralocorticoid and antiandrogen properties and are distinguished by a strong affinity for the gestagen receptor.

11β-Benzaldoximes of oestra-4,9-dien-3-ones are known from EP 0648778, EP 0648779 and EP 1060187. These compounds bind strongly to the progesterone receptor but much more weakly to the glucocorticoid receptor, and they exhibit both antigestagen and gestagen properties [Endocrine Rev. 2005, 26, 423-438]. As progesterone receptor modulators they are suitable for the treatment of a large number of gynaecological diseases [WO 01/34126, WO 01/15679, WO 01/44267].

The object of the present invention is to provide compounds with an antiglucocorticoid action which bind more strongly to the glucocorticoid receptor than to the progesterone receptor. They should therefore be capable of being used for the treatment and/or prevention of symptoms and/or diseases that are attributable to an androgen deficiency induced by glucocorticoids, especially cortisol.

Compared with the known compound RU 38486, the compounds according to the invention should be distinguished by a better dissociation between progesterone receptor and glucocorticoid receptor binding and be capable of displacing excess cortisol from the receptor, for example in order to compensate the corticoid-related drop in human testosterone level.

The object has been achieved according to the present invention by the 11β-benzaldoxime derivatives of D-homooestra-4,9-dienes of formula I:

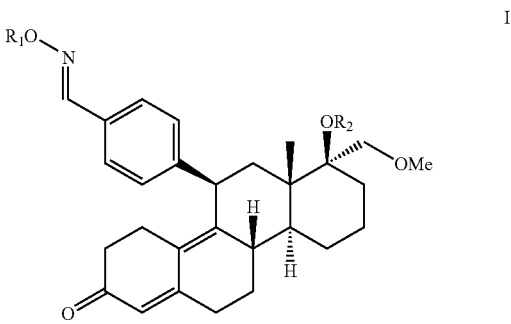

wherein
$R_1$ is a hydrogen atom or a $C_1$-$C_6$-alkyl, $C_1$-$C_6$-acyl, benzoyl, $C_1$-$C_4$-alkoxycarbonyl, $C_1$-$C_4$-alkylthiocarbonyl, $C_1$-$C_6$-alkylaminocarbonyl or arylaminocarbonyl group; and
$R_2$ is a hydrogen atom or a $C_1$-$C_6$-alkyl or $C_1$-$C_6$-acyl group, and their pharmaceutically acceptable salts.

The $C_1$-$C_6$-alkyl groups can be e.g. unbranched alkyl groups, such as a methyl, ethyl, propyl, butyl, pentyl or hexyl group, or branched $C_3$-$C_6$-alkyl groups, such as an isopropyl, isobutyl, sec-butyl, tert-butyl, isopentyl, 2-methylbutyl, 1-methylbutyl, 1-ethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl or 1,2-dimethylbutyl group.

The $C_1$-$C_6$-acyl groups for the radicals $R_1$ and $R_2$ can be e.g. a formyl, acetyl, propionyl, butyryl, isobutyryl, pentanoyl, isopentanoyl, pivaloyl or hexanoyl group.

A $C_1$-$C_4$-alkoxycarbonyl group is understood as meaning methoxycarbonyl [MeOC(O)—], ethoxycarbonyl [EtOC(O)—], n-propoxycarbonyl [CH$_3$CH$_2$CH$_2$OC(O)—], isopropoxycarbonyl [(CH$_3$)$_2$CHOC(O)—], n-butoxycarbonyl [CH$_3$CH$_2$CH$_2$CH$_2$OC(O)—], isobutoxycarbonyl [(CH$_3$)$_2$CHCH$_2$OC(O)—], sec-butoxy-carbonyl [CH$_3$CH$_2$(CH$_3$)CHOC(O)—] or tert-butoxycarbonyl [(CH$_3$)$_3$COC(O)—].

The $C_1$-$C_4$-alkylthiocarbonyl groups can be e.g. methylthiocarbonyl [MeSC(O)—], ethylthiocarbonyl [EtSC(O)—], n-propylthiocarbonyl [CH$_3$CH$_2$CH$_2$SC(O)—], isopropylthiocarbonyl [(CH$_3$)$_2$CHSC(O)—], n-butylthiocarbonyl [CH$_3$CH$_2$CH$_2$CH$_2$SC(O)—], isobutylthiocarbonyl [(CH$_3$)$_2$CHCH$_2$SC(O)—], sec-butylthiocarbonyl [CH$_3$CH$_2$(CH$_3$)CHSC(O)—] or tert-butylthiocarbonyl [(CH$_3$)$_3$CSC(O)—].

The $C_1$-$C_6$-alkylaminocarbonyl groups can be e.g. a methylaminocarbonyl, ethylaminocarbonyl, propylaminocarbonyl, isopropylaminocarbonyl, butylaminocarbonyl, isobutylaminocarbonyl, sec-butylaminocarbonyl, tert-butylaminocarbonyl, pentylaminocarbonyl, isopentylaminocarbonyl, (2-methylbutyl)aminocarbonyl, (1-methylbutyl)aminocarbonyl, (1-ethylpropyl)amino-carbonyl, neopentylaminocarbonyl, (1,1-dimethylpropyl)aminocarbonyl, hexylaminocarbonyl, (4-methylpentyl)aminocarbonyl, (3-methylpentyl)aminocarbonyl, (2-methylpentyl)aminocarbonyl, (1-methylpentyl)-aminocarbonyl, (1-ethylbutyl)aminocarbonyl, (2-ethylbutyl)aminocarbonyl, (3,3-dimethylbutyl)aminocarbonyl, (2,2-dimethylbutyl)aminocarbonyl, (1,1-dimethylbutyl)aminocarbonyl, (2,3-dimethylbutyl) aminocarbonyl, (1,3-dimethylbutyl)aminocarbonyl, (1, 2-dimethylbutyl)aminocarbonyl, pentyl-aminocarbonyl or hexylaminocarbonyl group.

The arylaminocarbonyl groups can be e.g. a phenylaminocarbonyl, (4-trifluoromethoxyphenyl)carbonyl or naphthylaminocarbonyl group.

Preferred compounds of general formula I according to the present invention are those in which $R_1$ is a hydrogen atom or a $C_1$-$C_4$-alkyl, $C_2$-$C_4$-acyl, benzoyl, $C_1$-$C_4$-alkoxycarbonyl, $C_1$-$C_4$-alkylthiocarbonyl, $C_1$-$C_4$-alkylaminocarbonyl, phenylaminocarbonyl or (4-trifluoromethoxyphenyl)aminocarbonyl group; and $R_2$ is a hydrogen atom or a methyl, ethyl or acetyl group.

The following are particularly preferred according to the present invention:

4-[17aβ-hydroxy-17aα-(methoxymethyl)-17a-homo-3-oxooestra-4,9-dien-11β-yl]benzaldehyde (1E)-oxime;

4-[17aβ-hydroxy-17aα-(methoxymethyl)-17a-homo-3-oxooestra-4,9-dien-11β-yl]benzaldehyde (1Z)-oxime;

4-[17aβ-methoxy-17aα-(methoxymethyl)-17a-homo-3-oxooestra-4,9-dien-11β-yl]benzaldehyde (1E)-oxime;

4-[17aβ-acetoxy-17aα-(methoxymethyl)-17a-homo-3-oxooestra-4,9-dien-11β-yl]benzaldehyde (1E)-oxime;

4-[17aβ-hydroxy-17aα-(methoxymethyl)-17a-homo-3-oxooestra-4,9-dien-11β-yl]benzaldehyde (1E)-(O-acetyl)oxime;

4-[17aβ-methoxy-17aα-(methoxymethyl)-17a-homo-3-oxooestra-4,9-dien-11β-yl]benzaldehyde (1E)-(O-acetyl)oxime;

4-[17aβ-hydroxy-17aα-(methoxymethyl)-17a-homo-3-oxooestra-4,9-dien-11β-yl]benzaldehyde (1E)-[O-(methoxy)carbonyl]oxime 4-[17aβ-methoxy-17aα-(methoxymethyl)-17a-homo-3-oxooestra-4,9-dien-11β-yl]benzaldehyde (1E)-[O-(methoxy)carbonyl]oxime;

4-[17aβ-methoxy-17aα-(methoxymethyl)-17a-homo-3-oxooestra-4,9-dien-11β-yl]benzaldehyde (1E)-[O-(ethoxy)carbonyl]oxime;

4-[17aβ-hydroxy-17aα-(methoxymethyl)-17a-homo-3-oxooestra-4,9-dien-11β-yl]benzaldehyde (1E)-[O-(ethoxy)carbonyl]oxime;

4-[17aβ-methoxy-17aα-(methoxymethyl)-17a-homo-3-oxooestra-4,9-dien-11β-yl]benzaldehyde (1E)-[O-(ethylthio)carbonyl]oxime;

4-[17aβ-methoxy-17aα-(methoxymethyl)-17a-homo-3-oxooestra-4,9-dien-11β-yl]benzaldehyde (1E)-[O-(ethylamino)carbonyl]oxime;

4-[17aβ-hydroxy-17aα-(methoxymethyl)-17a-homo-3-oxooestra-4,9-dien-11β-yl]benzaldehyde (1E)-[O-(ethylamino)carbonyl]oxime;

4-[17aβ-hydroxy-17aα-(methoxymethyl)-17a-homo-3-oxooestra-4,9-dien-11β-yl]benzaldehyde (1E)-{O-[(4'-trifluoromethoxy)phenylamino]carbonyl}oxime.

The compounds of general formula I according to the invention and their pharmaceutically acceptable salts are suitable for the preparation of pharmaceutical compositions and formulations. The pharmaceutical compositions or drugs contain as active ingredient at least one or more of the compounds of general formula I according to the invention or their acid addition salts, optionally in combination with other pharmacologically active substances. The drugs are prepared in known manner, it being possible to use the known and conventional pharmaceutical auxiliary substances and other conventional excipients and diluents.

Suitable inorganic acids for the formation of pharmaceutically acceptable salts of the compounds of general formula I according to the invention, by the methods known to those skilled in the art, are, inter alia, hydrochloric acid, hydrobromic acid, sulphuric acid, phosphoric acid and nitric acid, suitable carboxylic acids are, inter alia, acetic acid, propionic acid, hexanoic acid, octanoic acid, decanoic acid, oleic acid, stearic acid, maleic acid, fumaric acid, succinic acid, benzoic acid, ascorbic acid, oxalic acid, salicylic acid, tartaric acid, citric acid, lactic acid, glycolic acid, malic acid, mandelic acid, cinnamic acid, glutamic acid and aspartic acid, and suitable sulphonic acids are, inter alia, methanesulphonic acid, ethanesulphonic acid, toluenesulphonic acid, benzenesulphonic acid and naphthalenesulphonic acid.

Examples of suitable excipients and auxiliary substances are those recommended or indicated in the following literature references as auxiliary substances for pharmacy, cosmetics and related fields: Ullmann's Enzyklopädie der technischen Chemie (Ullmann's Encyclopaedia of Industrial Chemistry), 4, 1953, 1-39; J. Pharm. Sciences 52, 1963, 918 et seq.; H. v. Czetsch-Lindenwald, Hilfsstoffe für Pharmazie und angrenzende Gebiete (Auxiliary substances for pharmacy and related fields), Pharm. Ind. 2, 1961, 72 et seq.; Dr. H. P. Fiedler, Lexikon der Hilfsstoffe für Pharmazie, Kosmetik und angrenzende Gebiete (Glossary of auxiliary substances for pharmacy, cosmetics and related fields), Cantor K G, Aulendorf in Württemberg 1971.

The pharmaceutical preparations based on the novel compounds are formulated in a manner known per se by processing the active ingredient with the excipients, fillers, disintegration modifiers, binders, humectants, intestinal lubricants, absorbents, diluents, taste correctors, colourants, etc. that are conventionally used in galenics, and converting the product to the desired form of administration; cf. Remington's Pharmaceutical Science, 15th ed., Mack Publishing Company, East Pennsylvania (1980).

The preferred formulations consist of forms suitable for oral administration, examples of such forms of administration being tablets, film-coated tablets, dragees, capsules, pills, powders, solutions or suspensions, or also depot forms. The compounds of the general formula according to the invention, or the pharmaceutical compositions containing at least one of the compounds according to the invention, are preferably administered orally.

Appropriate tablets can be obtained e.g. by mixing the active ingredient with known auxiliary substances, for example inert diluents such as dextrose, sugar, sorbitol, mannitol or polyvinylpyrrolidone, disintegrants such as corn starch or alginic acid, binders such as starch or gelatin, intestinal lubricants such as magnesium stearate or talcum, and/or agents for achieving a depot effect, such as carboxypolymethylene, carboxymethyl cellulose, cellulose acetate-phthalate or polyvinyl acetate. The tablets can also consist of several layers. Correspondingly, dragees can be produced by coating cores (obtained analogously to the tablets) with agents conventionally used in dragee coatings, e.g. polyvinylpyrrolidone or shellac, gum arabic, talcum, titanium oxide or sugar. Again the dragee shell can consist of several layers, it being possible to use the auxiliary substances mentioned above for the tablets.

Solutions or suspensions containing the compounds of general formula I according to the invention can additionally contain taste improvers such as saccharin, cyclamate or sugar, as well as e.g. flavourings such as vanillin or orange extract. They can further contain suspension aids such as sodium carboxymethyl cellulose, or preservatives such as p-hydroxybenzoates.

Capsules containing the compounds of general formula I can be produced e.g. by mixing the compound of general formula I with an inert excipient such as lactose or sorbitol, and encapsulating the mixture in gelatin capsules.

The dosage of the amount of compounds to be administered varies within wide limits and can cover any effective amount.

Depending on the effect to be achieved and the type of administration, the amount of compound to be administered can range from 0.01 to 50 mg. A recommended daily dose for humans ranges from 0.05 to 10 mg.

Suitable dosages for the compounds according to the invention are from 0.1 to 10 mg. The compounds according to the invention are administered continuously, preferably once a day to once a week.

The invention also includes the compounds of general formula I according to the invention as therapeutic active ingredients, together with pharmaceutically compatible and acceptable auxiliary substances and/or excipients.

The invention also includes pharmaceutical compositions containing one of the pharmaceutically active compounds according to the invention, or a mixture thereof, or a pharmaceutically acceptable salt, together with pharmaceutically acceptable auxiliary substances and excipients.

Pharmacological Studies

Receptor Binding Affinity

The receptor binding affinity was determined by the competitive binding of a specifically binding $^3$H-labelled hormone (tracer) and the test compound to receptors in the cytosol from animal target organs, with the aim of achieving receptor saturation and reaction equilibrium.

The tracer and increasing concentrations of the test compound (competitor) were coincubated with the receptor-containing cytosol fraction at 0-4° C. for 18 h. After separation of the unbound tracer with a carbon/dextran suspension, the proportion of receptor-bound tracer was measured for each concentration and the $IC_{50}$ was determined from the concentration series. The relative molar binding affinity (RBA) was calculated as the quotient of the $IC_{50}$ values of reference substance and test compound (×100%) (RBA of reference substance=100%).

The following incubation conditions were chosen for the individual receptor types:

Progesterone Receptor:

Uterus cytosol of the oestradiol-primed rabbit, homogenized in TED buffer (20 mM Tris/HCl, pH 7.4; 1 mM ethylenediaminetetraacetate, 2 mM dithiothreitol) containing 250 mM sucrose; kept at −30° C. Tracer: $^3$H-ORG 2058, 5 nM; reference substance: progesterone.

Glucocorticoid Receptor:

Thymus cytosol of the adrenalectomized rat, thymi stored at −30° C.; buffer: TED. Tracer: $^3$H-dexamethasone, 20 nM; reference substance: dexamethasone.

Glucocorticoid/antiglucocorticoid Activity

The antagonistic activity of the compounds according to the invention on the glucocorticoid receptor was detected by means of transactivation experiments in HeLa cells.

HeLa-AGP-LUC cells were cultivated in DMEM (without phenol red), and 10% foetal calf serum (FCS), 2 mM L-glutamine, penicillin (100 U/ml), streptomycin (100 µg/ml) and geneticin (300 µg/ml) were added. The cells grew at 37° C. in a moist atmosphere and a 95/5% air/$CO_2$ mixture. One day before inoculation into the microtitre plate, the cells were transferred to an experimental medium (3% FCS treated with dextran/activated carbon in place of 10% FCS). The cells were inoculated into the microtitre plates (96-well) in a concentration of 10,000 cells/200 µl of experimental medium/well. The next day the cells were treated with 0.1-0.2% ethanol control or a glucocorticoid agonist, i.e. 10 nM DEX (6 replicates in each case). Prior to lysis (1 hour, shaking at 400 rpm) with lysis buffer (100 µl/well, Promega, catalogue number 3912), the cells were washed once with 200 µl of PBS/well.

The 11β-benzaldoxime derivatives of D-homooestra-4,9-dien-3-ones according to the invention are substances with an antiglucocorticoid action which bind to the glucocorticoid receptor better than the endogenous corticoids and the exogenous, very strongly binding glucocorticoid dexamethasone, but bind to the progesterone receptor less well than RU 38486. In respect of receptor binding, the compounds are dissociated better than RU 38486 (cf. Table 1).

TABLE 1

Receptor binding of selected compounds

| Compound | Progesterone receptor (PR) progesterone = 100% | Glucocorticoid receptor (GR) dexamethasone = 100% | Ratio GR/PR |
|---|---|---|---|
| Example 6 | 158% | 450% | 2.8 |
| Example 7 | 65% | 112% | 1.7 |
| RU 38486 | 506% | 683% | 1.3 |

Surprisingly, the compounds according to the invention exhibit a stronger binding to the glucocorticoid receptor, a weaker binding to the progesterone receptor and a better dissociation of the receptor values than RU 38486.

Compounds with this profile of action are suitable for the treatment and/or prophylaxis of diseases and/or symptoms that are attributable to an endogenous glucocorticoid-induced, especially age-related and/or stress-related cortisol-induced, androgen deficiency. They can be used for the treatment of glucocorticoid-related hypogonadism, sexual dysfunctions or infertility in men.

In contrast to the 11β-benzaldoximes of oestra-4,9-dien-3-ones of the state of the art, the compounds according to the invention surprisingly bind more strongly to the glucocorticoid receptor and prove to be antiglucocorticoids.

Moreover, the compounds according to the invention surprisingly bind selectively to the glucocorticoid receptor, thereby displacing the natural (endogenous) ligands of the glucocorticoid receptors, namely the glucocorticoids, without themselves having a glucocorticoid action. A selective antagonization of the glucocorticoid receptor takes place which reduces or else extensively prevents signal transmission via this receptor.

This reduction or prevention of occupation of the glucocorticoid receptors by glucocorticoid receptor antagonists is particularly useful when the endogenous glucocorticoid level is raised. Such an increase can be caused e.g. by age, a pathological increase in secretory activity of the adrenal cortex, physical or mental stress, and alcohol and drug abuse.

The glucocorticoid receptor antagonists according to the invention bind significantly less strongly to other steroid receptors, e.g. mineralocorticoid receptors, oestrogen receptors, progesterone receptors and androgen receptors. The expression "significantly less strongly" is understood as meaning that the binding to other steroid receptors has no practical effects.

Preparation of the Compounds According to the Invention

The present invention also provides a process for the preparation of the compounds comprising
  a) reaction of the compounds of formula II:

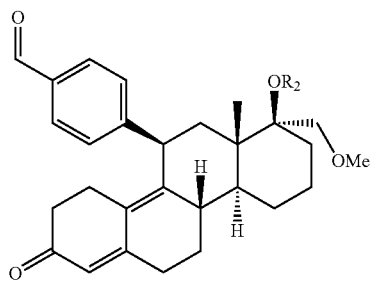

II with hydroxylamine or salts thereof, preferably the hydrochloride or hydrogen sulphate, in a solvent (e.g. pyridine, methanol, ethanol, tetrahydrofuran), optionally in the presence of an organic base (pyridine, triethylamine) or an inorganic base (e.g. NaOH, KOH, $NaHCO_3$, $KHCO_3$), to give compounds of formula Ia:

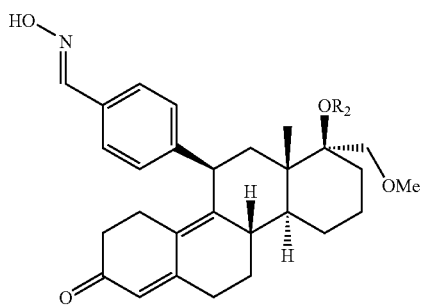

Ia and optionally
  b) reaction of the compounds of formula Ia with a reagent selected from the group comprising $C_1$-$C_6$-alkyl halides (e.g. $C_1$-$C_6$-alkyl chlorides, $C_1$-$C_6$-alkyl bromides or $C_1$-$C_6$-alkyl iodides), $C_1$-$C_6$-acyl halides (e.g. $C_1$-$C6$-acyl chlorides or $C_1$-$C_6$-acyl bromides), $C_1$-$C_6$-carboxylic anhydrides, benzoyl halides (e.g. benzoyl chloride), $C_1$-$C_4$-alkoxycarbonyl halides (e.g. methyl chloroformate), $C_1$-$C_4$-alkylthiocarbonyl halides (e.g. thioethyl chloroformate), $C_1$-$C_6$-alkylaminocarbonyl halides, $C_1$-$C_6$-alkyl isocyanates (e.g. ethyl isocyanate), arylaminocarbonyl halides and aryl isocyanates (e.g. 4-trifluoromethoxyphenyl isocyanate).

Preparation of Compounds of Formula II:

3-Methoxy-17a-D-homooestra-1,3,5(10)-trien-17a-one (III) [M. W. Goldberg, S. Studer, Helv. Chim. Acta 1941, 24, 295; J. Gutzwiller, W. Meier, A. Fürst, Helv. Chim. Acta 1977, 60, 2258-2269]:

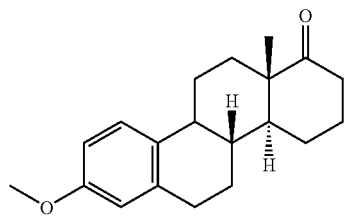

III is converted with trimethylsulphonium iodide and potassium tert-butanolate in dimethyl sulphoxide [E. J. Corey, M. Chaykowsky, J. Amer. Chem. Soc. 1962, 84: 3782-3783; G. Drefahl, K. Ponsold, H. Schick, Chem. Ber. 1964, 97, 3529-3535; C. E. Cook, R. C. Corley, M. E. Wall, J. Org. Chem. 1968, 33, 2789-2793] to a mixture of the 17(R)- and 17(S)-spiroepoxides (IV):

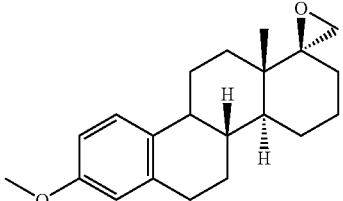

IVa

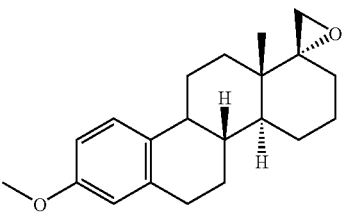

IVb which, without further separation, is reacted with sodium methylate (EP 0411733) to give a mixture of Va and Vb. The resulting mixture is then separated, e.g. by chromatographic purification.

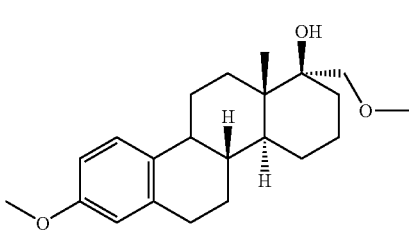

Va

Vb

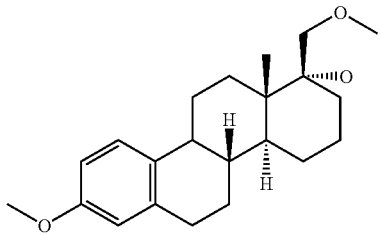

Compound Va is then subjected to a Birch reduction (A. J. Birch, R. J. Harrison, Austral. J. Chemistry 1995, 8, 515) to give the dienol derivative VIa:

VIa

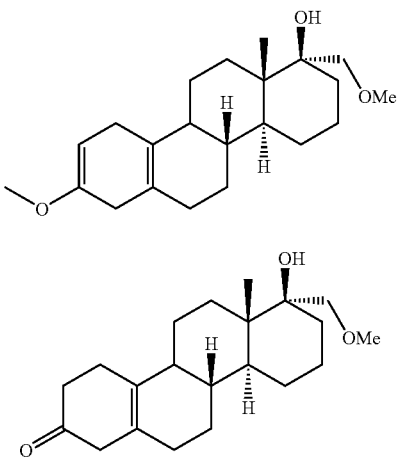

VIb

In a manner known per se, the treatment of VIa with dilute acid yields the 3-keto -5(10)-ene derivative VIb, which is subjected to a bromination/dehydrobromination in pyridine [M. Perelmann, E. Farkas, J. Amer. Chem. Soc. 1960, 82, 2402] to give the 3-keto4,9-diene derivative VIIIa:

VIIIa

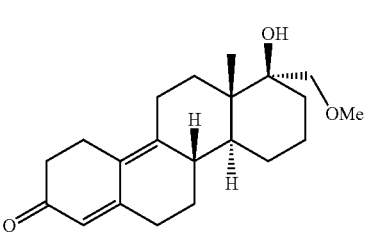

Conversion of the 4,9-diene VIIIa to the 5(10),9(11)-diene IXa requires an acetalization in the 3-position. The acetalization can take place either with methanol to give the dimethyl acetal, or with ethane-1,2-diol to give the 3-ethylene ketal, or with dimethylpropanediol to give the 3-neopentyl ketal. For example, compound VIIIa can be reacted with ethanediol and acid to give the ethylene ketal IXa in good yields. The 17β-hydroxy group can then be etherified (e.g. to IXb) or esterified.

IXa

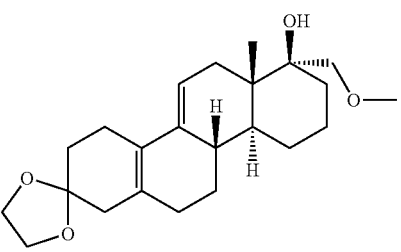

IXb

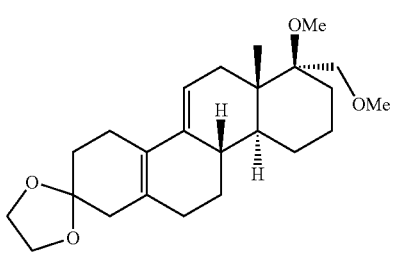

Subsequent epoxidation of the diene system of IX with hexafluoroacetone and $H_2O_2$ [C. T. Ratcliffe, C. V. Hardin, L. R. Anderson, W. B. Fox, J. Chem. Soc. Chem. Commun. 1971, 784; Gasc (1974) Fr. Pat. 2201287; R. Rhode, G. Neef, G. Sauer, R. Wiechert, Tetrahedron Letters 1984, 26, 2069-2072] yields an approx. 4:1 mixture of the 5α,10α- and 5β,10β-epoxides X and XI if $R_2$ is a hydrogen atom or an alkyl or acyl group.

X

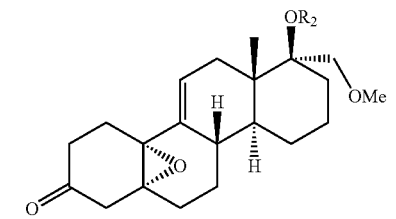

XI

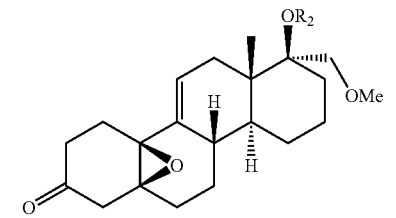

The 11-aryl radical is introduced by means of a transition metal-catalysed Grignard reaction with opening of the epoxide [G. Teutsch, A. Belanger, Tetrahedron Letters 1979, 30, 2051-2054] and rearrangement of the initially formed 10-aryl derivative to the 11-position. Thus the reaction of Xa ($R_2$=H) with bromobenzaldehyde ethylene ketal in the presence of Cu(I) salts [CuCl or CuI] gives the compound XII substituted on C-11, the α-epoxide yielding the corresponding 11β-aryl derivative and the β-epoxide XII yielding the corresponding 11α-aryl derivative.

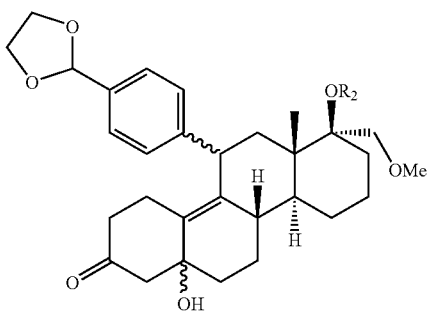

XII

Acid hydrolysis of the mixture of XII yields a mixture of the 11β- and 11α-benzaldehydes II and XIII, from which the compound II having the 11β configuration can be separated by recrystallization.

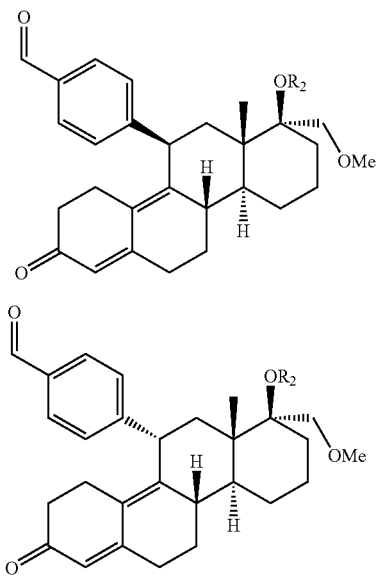

II

XIII

EXAMPLES

Example 1

4-[17aβ-Hydroxy-17aα-(methoxymethyl)-17a-homo-3-oxooestra-4,9-dien-11β-yl]benzaldehyde (1E)-oxime 956 mg of 4-[17aβ-hydroxy-17aα-(methoxymethyl)-17a-homo-3-oxooestra-4,9-dien-11β-yl]benzaldehyde are dissolved in 10 ml of pyridine. 205 mg of hydroxylamine hydrochloride are added in portions under an argon blanket. After 4 hours the mixture is stirred into 500 ml of ice-water to precipitate the substance. The precipitate is filtered off with suction, washed with water, with dilute HCl and with water until the washings are neutral, and dried in air. After extraction with methylene chloride and evaporation of the solvent, 955 mg of crude product remain. This is purified by chromatography to give 550 mg of 4-[17aβ-hydroxy-17aα-(methoxymethyl)-17a-homo-3-oxooestra-4, 9-dien-11β-yl]benzaldehyde (1E)-oxime as an amorphous product:

$α_D$=+193° (CHCl$_3$) $^1$H NMR (400 MHz, CDCl$_3$, δ in ppm with TMS as internal standard): 0.50 (s, 3H, H-18), 2.18 (s, 1H, OH), 3.12 and 3.53 (2d, 2H, J=8.4 Hz, CH$_2$O), 3.41 (s, 3H, OCH$_3$), 4.37 (d, 1H, J=6.4 Hz, H-11α), 5.76 (s, 1H, H-4), 7.19 (d, 2H, J=8.4 Hz, CH-arom.), 7.48 (d, 2H, J=8.4 Hz), 8.10 (s, 1H, CH=N), 8.55 (s, 1H, NOH) MS (m/e, 70 eV): 449.25518 (M$^+$), 431.24438 (M$^+$–H$_2$O, 100%);

and 187 mg of 4-[17aβ-hydroxy-17aα-(methoxymethyl)-17a-homo-3-oxooestra-4,9-dien-11β-yl]benzaldehyde (1Z)-oxime.

Preparation of the Starting Compound of Example 1

4-[17aβ-Hydroxy-17aα-(methoxymethyl)-17a-homo-3-oxooestra-4,9-dien-11β-yl]benzaldehyde Stage A:

17a-(S)-Spiroepoxy-17a-homooestra-1,3,5(10)-triene 3-methyl ether 22 g of trimethylsulphonium iodide and, in portions, 11.6 g of potassium tert-butanolate are added to a solution of 16.1 g of 3-methoxy-17a-homooestra-1,3,5(10)-trien-17a-one in 500 ml of DMSO at 10° C. under an argon blanket. The mixture is stirred for 2 hours at room temperature and poured into 1.5 l of ice-water, the precipitate is extracted with methylene chloride, the organic phase is washed with water, dried over sodium sulphate and filtered and the solution is evaporated under vacuum to give 15.4 g of crude product, which is used in the next stage.

For analysis, 240 mg are purified by preparative layer chromatography to give 120 mg of 17a-(R)-spiroepoxy-17a-homooestra-1,3,5(10)-triene 3-methyl ether:

M.p.: 82 to 86° C. (methanol) $α_D$=+13° (CHCl$_3$) $^1$H NMR (300 MHz, CDCl$_3$, δ in ppm with TMS as internal standard): 1.06 (s, 3H, H-18), 2.45 and 3.10 (2d, 2H, J=4.5 Hz, CH$_2$O), 3.78 (s, 3H, OCH$_3$), 6.63, 6.7 and 7.20 (3H, CH-arom.);

and 54 mg of 17a-(S)-spiroepoxy-17a-homooestra-1,3,5(10)-triene 3-methyl ether:

M.p.: 142 to 148° C. (methanol) $α_D$=+39° (CHCl$_3$) $^1$H NMR (300 MHz, CDCl$_3$, δ in ppm with TMS as internal standard): 1.05 (s, 3H, H-18), 2.41 and 2.88 (2d, 2H, J=4.5 Hz, 17-CH$_2$O), 3.78 (s, 3H, OCH$_3$), 6.62, 6.7 and 7.21 (CH-arom.).

Stage B:

3-Methoxy-17aα-(methoxymethyl)-17a-homooestra-1,3,5(10)-trien-17aβ-ol 32.4 g of sodium methylate are added to 15.1 g of 17a-(R,S)-spiroepoxy-17a-homooestra-1,3,5(10)-triene 3-methyl ether mixture (from stage A) in 500 ml of DMSO and the resulting mixture is stirred for 5 hours at 95° C. It is cooled and poured into 1.7 l of ice-water and the precipitate is filtered off with suction, washed with water and dried in air. The crude product (16.2 g) is purified by chromatography on silica gel to give 6.34 g of 3-methoxy-17aα-(methoxymethyl)-17a-homooestra-1, 3,5(10)-trien-17aβ-ol:

M.p.: 128 to 129° C. (methanol) $α_D$=+44° (CHCl$_3$) $^1$H NMR (300 MHz, CDCl$_3$, δ in ppm with TMS as internal standard): 0.88 (s, 3H, H-18), 3.20 and 3.51 (2d, 2H, J=8.7 Hz, 17-CH$_2$O), 3.40 (s, 3H, OCH$_3$), 3.78 (s, 3H, OCH$_3$), 6.62, 6.7 and 7.2 (CH-arom.) HPLC: 99.9 area % at 278 nm;

and 3.1 g of 3-methoxy-17aβ-(methoxymethyl)-17a-homooestra-1,3,5(10)-trien-17aα-ol:

M.p.: 162 to 163° C. (methanol) $α_D$=+48° (CHCl$_3$) $^1$H NMR (300 MHz, CDCl$_3$, δ in ppm with TMS as internal standard): 1.02 (s, 3H, H-18), 2.34 (s, 1H, OH), 3.42 (s, 3H, OCH$_3$), 3.62 (s, 2H, 17-CH$_2$O), 3.78 (s, 3H, arom.-OCH$_3$), 6.62, 6.7 and 7.2 (CH-arom.).

Stage C:

3-Methoxy-17aα-(methoxymethyl)-17a-homooestra-2,5(10)-dien-17aβ-ol 300 ml of ammonia are condensed under an argon blanket and cooled to –60° C. 10 ml of abs. THF are added, the mixture is stirred for 10 minutes and the solution is coloured blue by adding sodium in portions. 60 ml of a solution consisting of 70 ml of abs. THF, 16 ml of methoxypropanol and 3.49 g of 3-methoxy-17aα-(methoxymethyl)-17a-homooestra-1,3,5(10)-trien-17aβ-ol are added dropwise to this solution. The resulting solution decolourizes after a while and sodium is added in portions until the solution remains a stable blue colour for 30 minutes. After 3 hours the reaction is stopped by adding ammonium chloride (solid) and the ammonia is evaporated off. 5 ml of isopropanol are added, the mixture is stirred for a further 15 minutes and a colourless precipitate is produced by adding water. This is filtered off with suction, washed with water and dried to give 3.45 g of 3-methoxy-17aα-(methoxymethyl)-17a-homooestra-2,5(10)-dien-17aβ-ol:

M.p.: 144 to 146° C. (acetone) $α_D$=+96° (CHCl$_3$) $^1$H NMR (300 MHz, CDCl$_3$, δ in ppm with TMS as internal standard): 0.87 (s, 3H, H-18), 2.28 (s, 1H, OH), 3.19 and 3.48 (2d, 2H, J=8.7 Hz, CH$_2$O), 3.38 (s, 3H, OCH$_3$), 3.55 (s, 3H, arom.-OCH$_3$), 4.65 (m, 2H, H-4).

Stage D:

17aβ-Hydroxy-17aα-(methoxymethyl)-17a-homooestra-5(10)-en-3-one 3.2 g of 3-methoxy-17aα-(methoxymethyl)-17a-homooestra-2,5(10)-dien-17aβ-ol are dissolved in 50 ml of methylene chloride, 160 ml of tert-butanol and 50 ml of a mixture of 60 ml of water and 0.24 ml of 60% perchloric acid are added and the mixture is stirred for 5 hours at room temperature. The pH is adjusted to 8 with aqueous sodium bicarbonate solution, the phases are separated and the organic phase is washed with water, dried over sodium sulphate, filtered and evaporated under vacuum to give 3.1 g of crude product:

M.p.: 160 to 162° C. (methylene chloride/tert-butyl methyl ether) $α_D$=+158° (CHCl$_3$) $^1$H NMR (300 MHz, CDCl$_3$, δ in ppm with TMS as internal standard): 0.88 (s, 3H, H-18), 2.30 (s, 1H, OH), 2.7 (q, 2H, H-4), 3.19 and 3.48 (2d, 2H, J=8.7 Hz, CH$_2$O), 3.38 (s, 3H, OCH$_3$).

Stage E:

17aβ-Hydroxy-17aα-(methoxymethyl)-17a-homooestra-4,9-dien-3-one 7.3 g of 17aβ-hydroxy-17aα-(methoxymethyl)-17a-homooestra-5(10)-en-3-one are dissolved in 115 ml of pyridine and cooled to –70° C. 7.0 g of pyridinium bromide perbromide are added and the reaction mixture is removed from the cooling bath, stirred for 20 hours at room temperature and decomposed with ice-water. The precipitate is filtered off with suction, washed with water and dried to give 5.8 g of crude product. This is purified by chromatography on silica gel with a toluene/acetone gradient to give 4.9 g of 17aβ-hydroxy-17aα-(methoxymethyl)-17a-homooestra-4,9-dien-3-one:

M.p.: 164 to 166° C. (acetone) $α_D$=–343° (CHCl$_3$) $^1$H NMR (300 MHz, CDCl$_3$, δ in ppm with TMS as internal standard): 1.02 (s, 3H, H-18), 2.31 (s, 1H, OH), 3.20 and 3.49 (2d, 2H, J=8.7 Hz, CH$_2$O), 3.39 (s, 3H, OCH$_3$), 4.37 (d, 1H, J=6.4 Hz, H-11α), 5.65 (s, 1H, H-4) GC/MS: 99.6 area % at M$^+$+1=331.

Stage F:

3,3-Ethylenedioxy-17aα-(methoxymethyl)-17a-homooestra-5(10),9(11)-dien-17aβ-ol 8.6 g of 17aβ-hydroxy-17aα-(methoxymethyl)-17a-homooestra-4,9-dien-3-one in 35 ml of methylene chloride are stirred with 7 ml of ethylene glycol, and 2.2 ml of trimethylchlorosilane are added in portions. After 5 hours the mixture is stirred into aqueous sodium bicarbonate solution, the phases are separated and the organic phase is washed with water until the washings are neutral, dried over sodium sulphate, filtered and evaporated under vacuum. The crude product (9.9 g) is purified by chromatography on silica gel with a toluene/acetone gradient.

Yield: 8.5 g (foam from acetone/n-hexane): $α_D$=+68° (CHCl$_3$) $^1$H NMR (300 MHz, CDCl$_3$, δ in ppm with TMS as internal standard): 0.81 (s, 3H, H-18), 2.26 (s, 1H, OH), 3.23 and 3.44 (2d, 2H, J=8.7 Hz, CH$_2$O), 3.39 (s, 3H, OCH$_3$), 3.98 (s, 4H, ethylene ketal), 5.59 (m, 1H, H-11).

Stage G:

5α,10α-Epoxy-3,3-ethylenedioxy-17aα-(methoxymethyl)-17a-homooestra-9(11)-dien-17aβ-ol 8.4 g of 3,3-ethylenedioxy-17aα-(methoxymethyl)-17a-homooestra-5(10),9(11)-dien-17aβ-ol are dissolved in 85 ml of methylene chloride, and 2.1 ml of pyridine are added. The mixture is cooled to 0° C., 2.1 ml of hexafluoroacetone sesquihydrate are added and 8.5 ml of 50% H$_2$O$_2$ are then added dropwise. The mixture is stirred for 3 hours at room temperature, 20 ml of aqueous sodium bicarbonate solution are added and the phases are separated. The organic phase is washed with 35% sodium thiosulphate solution, with sodium chloride solution and with water, dried over sodium sulphate, filtered and concentrated under vacuum. The crude product is purified by column chromatography:

M.p.: 171 to 173° C. (acetone) $α_D$=–31° (CHCl$_3$) $^1$H NMR (400 MHz, CDCl$_3$, δ in ppm with TMS as internal standard): 0.82 (s, 3H, H-18), 2.23 (s, 1H, OH), 3.21 and 3.39 (2d, 2H, J=8.8 Hz, CH$_2$O), 3.37 (s, 3H, OCH$_3$), 3.86-3.95 (m, 4H, ethylene ketal), 6.03 (d, 1H, J=6.0 Hz, H-11) LC/MS: 98.75 area % at M$^+$+1=391; 373 (M$^+$–H$_2$O, 100%).

Stage H:

4-[3,3-Ethylenedioxy-5α,17aβ-dihydroxy-17aα-(methoxymethyl)-17a-homooestra-9-en-11β-yl]benzaldehyde dimethyl ketal 300 mg of CuCl are added to a Grignard solution (prepared from 700 mg of magnesium in 10 ml of abs. THF and 6.7 g of bromobenzaldehyde dimethyl acetal in 3 ml of abs. THF) and the solution is cooled to –30° C. A solution of 2.25 g of 5α,10α-epoxy-3,3-ethylenedioxy-17aα-(methoxymethyl)-17a-homooestra-9(11)-dien-17aβ-ol in 15 ml of abs. THF is added dropwise at this temperature and the mixture is stirred for 20 minutes at this temperature and then allowed to warm up to room temperature. After one hour it is decomposed with aqueous ammonium chloride solution, ethyl acetate is added and the organic phase is washed until the washings are neutral, dried and concentrated under vacuum to give 6.6 g of an oil, which is purified by chromatography. Yield: 2.3 g of a colourless resin, which is used without further purification for hydrolysis of the protecting groups:

$\alpha_D$=−5° (CHCl$_3$) $^1$H NMR (400 MHz, CDCl$_3$, δ in ppm with TMS as internal standard): 0.41 (s, 3H, H-18), 2.20 (s, 1H, OH), 3.07 and 3.48 (2d, 2H, J=8.4 Hz, CH$_2$O), 3.31, 3.32 (2s, 3H each, 2×OCH$_3$), 3.37 (s, 3H, CH$_2$OCH$_3$), 3.90-3.99 (m, 4H, ethylene ketal), 4.11 (s, 1H, 5-OH), 4.26 (d, 1H, J=6.8 Hz, H-11α), 5.35 (s, 1H, CH-ketal), 7.20 (d, 2H, J=8.0 Hz, CH-arom.), 7.31 (d, 2H, J=8.0 Hz).

Stage I:

4-[17aβ-Hydroxy-17aα-(methoxymethyl)-17a-homo-3-oxooestra-4,9-dien-11β-yl]benzaldehyde 2.25 g of 4-[3,3-ethylenedioxy-5α,17aβ-dihydroxy-17aα-(methoxymethyl)-17a-homooestra-9-en-11β-yl]benzaldehyde dimethyl ketal are dissolved in 25 ml of acetone, and 2.5 ml of water and 820 mg of p-toluenesulphonic acid are added. The mixture is stirred for 1.5 hours at room temperature and poured into 600 ml of ice-water and the precipitate obtained is filtered off with suction, washed with water, with aqueous sodium bicarbonate solution and with water and dried in air. The crude product (1.81 g) is purified by chromatography. Yield: 1.43 g of 4-[17aβ-hydroxy-17aα-(methoxymethyl)-17a-homo-3-oxooestra-4,9-dien-11β-yl]-benzaldehyde:

M.p.: 87 to 90° C. (acetone) $\alpha_D$=+161° (CHCl$_3$) $^1$H NMR (400 MHz, CDCl$_3$, δ in ppm with TMS as internal standard): 0.48 (s, 3H, H-18), 3.11 and 3.52 (2d, 2H, J=8.8 Hz, CH$_2$O), 3.41 (s, 3H, OCH$_3$), 4.43 (d, 1H, J=6.8Hz, H-11α), 5.76 (s, 1H, H-4), 7.37 (d, 2H, J=8.0Hz, CH-arom.), 7.80 (d, 2H, J=8.0 Hz), 9.96 (s, 1H, CH=O) GC/MS: 99.9 area % at M$^+$+1=435.

Example 2

4-[17aβ-Hydroxy-17aα-(methoxymethyl)-17a-homo-3-oxooestra-4,9-dien-11β-yl]benzaldehyde (1E)-[O-(ethylamino)carbonyl]oxime 365 mg of 4-[17aβ-hydroxy-17aα-(methoxymethyl)-17a-homo-3-oxooestra-4,9-dien-11β-yl]benzaldehyde (1E)-oxime are dissolved in 15 ml of toluene. 0.25 ml of ethyl isocyanate in 2 ml of toluene is added dropwise under an argon blanket, the mixture is stirred for 2 hours at room temperature, a further 0.5 ml of ethyl isocyanate is added and the mixture is heated for 3 hours at 50° C., allowed to cool and stirred for a further 10 hours at room temperature. The reaction mixture is decomposed by adding aqueous ammonia solution, the phases are separated and the organic phase is washed until the washings are neutral, dried and evaporated under vacuum to give 379 mg of a colourless crude product, which is purified by preparative layer chromatography on silica gel PF$_{254\ nm}$ with tert-butyl methyl ether. 237 mg of 4-[17aβ-hydroxy-17aα-(methoxymethyl)-17a-homo-3-oxooestra-4,9-dien-11β-yl]benzaldehyde (1E)-[O-(ethylamino)carbonyl]oxime are obtained as an amorphous product from acetone/n-hexane:

$\alpha_D$=+207° (CHCl$_3$) $^1$H NMR (400 MHz, CDCl$_3$, δ in ppm with TMS as internal standard): 0.50 (s, 3H, H-18), 1.23 (t, 3H, CH$_2$CH$_3$), 3.12 and 3.52 (2d, 2H, J=8.8 and 9.2 Hz, CH$_2$O), 3.39 (m, 2H, CH$_2$), 3.41 (s, 3H, OCH$_3$), 4.39 (d, 1H, J=6.8Hz, H-11α), 5.76 (s, 1H, H-4), 6.22 (t, 1H, NH), 7.26 (d, 2H, J=8.0 Hz, CH-arom.), 7.59 (d, 2H, J=8.0 Hz), 8.29 (s, 1 H, CH=NOCO) LC/MS: M$^+$+1=521;

and 75 mg of 4-[17aβ-hydroxy-17aα-(methoxymethyl)-17a-homo-3-oxooestra-4,9-dien-11β-yl]benzonitrile (4811) are obtained as an amorphous product from tert-butyl methyl ether/cyclohexane:

$\alpha_D$=+151° (CHCl$_3$) $^1$H NMR (400 MHz, CDCl$_3$, δ in ppm with TMS as internal standard): 0.46 (s, 3H, H-18), 3.11 and 3.52 (2d, 2H, J=8.4 Hz, CH$_2$O), 3.41 (s, 3H, OCH$_3$), 4.39 (d, 1H, J=7.2 Hz, H-11α), 5.76 (s, 1H, H-4), 7.30 (d, 2H, J=8.0 Hz, CH-arom.), 7.57 (d, 2H, J=8.0 Hz) IR: 2224 cm$^{-1}$ (C≡N) LC/MS: M$^+$+1=521.

Example 3

0.6 ml of 4-trifluoromethoxyphenyl isocyanate in 2 ml of toluene is added dropwise under an argon blanket to 225 mg of 4-[17aβ-hydroxy-17aα-(methoxymethyl)-17a-homo-3-oxooestra-4,9-dien-11β-yl]benzaldehyde (1E)-oxime in 10 ml of toluene. The mixture is stirred for 3 hours at room temperature, 20 ml of aqueous ammonia solution are added and the mixture is stirred for a further 1 hour. The phases are separated by dilution with methylene chloride and the organic phase is washed until the washings are neutral, dried and evaporated under vacuum to give 865 mg of a foam, which is purified by chromatography. 115 mg of 4-[17aβ-hydroxy-17aα-(methoxymethyl)-17a-homo-3-oxooestra-4,9-dien-11β-yl]benzaldehyde (1E)-{O-[(4'-trifluoromethoxy)phenylamino]carbonyl}oxime are isolated as an amorphous product from tert-butyl methyl ether/cyclohexane:

$\alpha_D$=+178° (CHCl$_3$) $^1$H NMR (400 MHz, CDCl$_3$, δ in ppm with TMS as internal standard): 0.51 (s, 3H, H-18), 1.23 (t, 3H, CH$_2$CH$_3$), 3.12 and 3.52 (2d, 2H, J=8.4 and 8.8 Hz, CH$_2$O), 3.41 (s, 3H, OCH$_3$), 4.41 (d, 1H, J=6.4 Hz, H-11α), 5.76 (s, 1H, H-4), 6.22 (t, 1H, NH), 7.21 (d, 2H, J=8.4 Hz, CH-arom.) and 7.54 (d, 2H, J=8.8 Hz), 7.30 (d, 2H, J=8.0 Hz, CH-arom.) and 7.64 (d, 2H, J=8.4 Hz), 8.17 (s, 1H, NH), 8.37 (s, 1H, CH=NOCO) LC/MS: M$^+$+1=653.

Example 4

4-[17aβ-Hydroxy-17aα-(methoxymethyl)-17a-homo-3-oxooestra-4,9-dien-11β-yl]benzaldehyde (1E)-oxime acetate 4 ml of a 1:1 (v/v) mixture of acetic anhydride and pyridine are added to 200 mg of 4-[17aβ-hydroxy-17aα-(methoxymethyl)-17a-homo-3-oxooestra-4,9-dien-11β-yl]-benzaldehyde (1E)-oxime. After 4 hours the mixture is diluted with water and extracted with CH$_2$Cl$_2$ and the extract is washed until the washings are neutral, dried over Na$_2$SO$_4$, filtered and concentrated under vacuum. After purification by preparative layer chromatography on silica gel, 135 mg of 4-[17aβ-hydroxy-17aα-(methoxymethyl)-17a-homo-3-oxooestra-4,9-dien-11β-yl]benzaldehyde (1E)-oxime acetate are isolated as a colourless foam:

$\alpha_D$=+182° (CHCl$_3$) $^1$H NMR (400 MHz, CDCl$_3$, δ in ppm with TMS as internal standard): 0.51 (s, 3H, H-18), 2.07 (s, 3H, COCH$_3$), 3.42 and 3.54 (2d, 2H, J=8.4 and 8.8 Hz, CH$_2$O), 4.41 (d, 1H, J=6.8 Hz, H-11α), 5.78 (s, 1H, H-4), 7.24 (d, 2H, J=8.0 Hz, CH-arom.) and 7.63 (d, 2H, J=8.4 Hz), 8.32 (s, 1H, CH=N—R).

Example 5

4-[17aβ-Methoxy-17aα-(methoxymethyl)-17a-homo-3-oxooestra-4,9-dien-11β-yl]benzaldehyde (1E)-oxime 5.2 g of 4-[17aβ-methoxy-17aα-(methoxymethyl)-17a-homo-3-oxooestra-4,9-dien-11β-yl]benzaldehyde are reacted with 970 mg of hydroxylamine hydrochloride in 50 ml of pyridine analogously to Example 1, worked up and purified to give 4.1 g of 4-[17aβ-methoxy-17aα-(methoxymethyl)-17a-homo-3-oxooestra-4,9-dien-11β-yl]benzaldehyde (1E)-oxime:

M.p.: 148° C. (methyl tert-butyl ether) $^1$H NMR (400 MHz, CDCl$_3$, δ in ppm with TMS as internal standard): 0.57 (s, 3H, H-18), 3.12 and 3.53 (2d, 2H, J=8.4 Hz, CH$_2$O), 3.26, 3.37 (2s, 6H, OCH$_3$), 4.33 (d, 1H, J=6.0 Hz, H-11α), 5.74 (s, 1H, H-4), 7.20 (d, 2H, J=8.4 Hz, CH-arom.), 7.49 (d, 2H, J=8.4 Hz), 7.85 (s, 1H, NOH), 8.10 (s, 1H, CH=N).

Preparation of the Starting Compound of Example 5

Stage A:

4-[3,3-Ethylenedioxy-5α, 17aβ-dimethoxy-17aα-(methoxymethyl)-17a-homooestra-9-en-11β-yl]benzaldehyde dimethyl ketal 784 mg of potassium tert-butanolate are added to 1.08 g of 4-[3,3-ethylenedioxy-5α, 17aβ-dihydroxy-17aα-(methoxymethyl)-17a-homooestra-9-en-11β-yl]benzaldehyde dimethyl ketal (Example 1, stage H) in 40 ml of toluene. The mixture is stirred for 10 minutes at room temperature, 3 ml of methyl iodide are added, the mixture is stirred until the reaction is complete, and decomposed with water, the phases are separated and the organic phase is washed until the washings are neutral, dried, filtered and concentrated under vacuum. The crude product is used without further purification for hydrolysis of the protecting groups:

$^1$H NMR (400 MHz, CDCl$_3$, δ in ppm with TMS as internal standard): 0.50 (s, 3H, H-18), 3.22, 3.23 (2s, 3H each, 2×OCH$_3$), 3.31, 3.32 (3s, 3×OCH$_3$, 5,17,17-CH$_2$), 3.37 (s, 2H, CH$_2$O), 3.78-4.02 (m, 4H, ethylene ketal), 4.21 (d, 1H, J=6.8 Hz, H-11α), 5.35 (s, 1H, CH-ketal), 7.20 (d, 2H, J=8.0 Hz, CH-arom.), 7.30 (d, 2H, J=8.0 Hz, CH-arom.).

Stage B:

4-[17aβ-Methoxy-17aα-(methoxymethyl)-17a-homo-3-oxooestra-4,9-dien-11β-yl]benzaldehyde 8 g of 4-[3,3-ethylenedioxy-5α-hydroxy-17aβ-methoxy-17aα-(methoxymethyl)-17a-homooestra-9-en-11β-yl]benzaldehyde dimethyl ketal are reacted with 25 ml of water and 6 g of p-toluenesulphonic acid in 250 ml of acetone analogously to Example 1. Yield: 5 g of 4-[17aβ-methoxy-17aα-(methoxymethyl)-17a-homo-3-oxooestra-4,9-dien-11β-yl]benzaldehyde as a crystalline residue:

α$_D$=+129° (CHCl$_3$) $^1$H NMR (400 MHz, CDCl$_3$, δ in ppm with TMS as internal standard): 0.55 (s, 3H, H-18), 3.26 (s, 3H, OCH$_3$), 3.35 (s, 3H, OCH$_3$), 3.38 (d, 2H, J=3.6 Hz, CH$_2$O), 4.38 (d, 1H, J=6.0 Hz, H-11α), 5.75 (s, 1H, H-4), 7.35 (d, 2H, J=8.4 Hz, CH-arom.), 7.79 (d, 2H, J=8.4 Hz), 9.96 (s, 1H, CH=O).

Example 6

4-[17aβ-Methoxy-17aα-(methoxymethyl)-17a-homo-3-oxooestra-4,9-dien-11β-yl]benzaldehyde (1E)-[O-(ethylamino)carbonyl]oxime 1.1 g of 4-[17aβ-methoxy-17aα-(methoxymethyl)-17a-homo-3-oxooestra-4,9-dien-11β-yl]benzaldehyde (1E)-oxime are dissolved in 16 ml of toluene at room temperature and 1.6 ml of triethylamine and 0.65 ml of ethyl isocyanate are added. The solution is heated at 65° C. for 3 hours and allowed to cool to room temperature. The reaction mixture is decomposed by adding aqueous ammonia solution, the phases are separated and the organic phase is washed until the washings are neutral, dried and evaporated under vacuum. The product is purified by recrystallization from ethyl acetate to give 0.7 g of 4-[17aβ-methoxy-17aα-(methoxymethyl)-17a-homo-3-oxooestra-4,9-dien-11β-yl]benzaldehyde (1E)-[O-(ethylamino)carbonyl]oxime:

$^1$H NMR (400 MHz, CDCl$_3$, δ in ppm with TMS as internal standard): 0.55 (s, 3H, H-18), 1.23 (t, 3H, CH$_2$CH$_3$), 3.10 and 3.55 (2d, 2H, J=8.4 Hz, CH$_2$O), 3.26, 3.37 (2s, 6H, OCH$_3$), 4.31 (d, 1H, J=6.2 Hz, H-11α), 5.73 (s, 1H, H-4), 6.23 (t, 1H, NH), 7.20 (d, 2H, J=8.2 Hz, CH-arom.), 7.50 (d, 2H, J=8.4 Hz), 8.29 (s,1 H, CH=NOCO).

Example 7

4-[17aβ-Methoxy-17aα-(methoxymethyl)-17a-homo-3-oxooestra-4,9-dien-11β-yl]benzaldehyde (1E)-[O-(ethylthio)carbonyl]oxime 1.1 g of 4-[17aβ-methoxy-17aα-(methoxymethyl)-17a-homo-3-oxooestra-4,9-dien-11β-yl]benzaldehyde (1E)-oxime are dissolved in 15 ml of pyridine and cooled to 0° C. 1.3 ml of thioethyl chloroformate are then added dropwise, without further cooling, and the mixture is stirred for 3 hours. 30 ml of ethyl acetate are then added and the solution is cooled to 10° C. The pH is adjusted to 2 with 10% hydrochloric acid, the phases are separated and the organic phase is washed until the washings are neutral, dried and evaporated under vacuum. The product is purified by recrystallization from methyl tert-butyl ether to give 0.8 g of 4-[17aβ-methoxy-17aα-(methoxymethyl)-17a-homo-3-oxooestra-4,9-dien-11β-yl]benzaldehyde (1E)-[O-(ethylthio)carbonyl]oxime:

$^1$H NMR (400 MHz, CDCl$_3$, δ in ppm with TMS as internal standard): 0.58 (s, 3H, H-18), 1.38 (t, 3H, CH$_2$CH$_3$), 3.12 and 3.58 (2d, 2H, J=8.0 Hz, CH$_2$O), 3.24, 3.36 (2s, 6H, OCH$_3$), 4.41 (d, 1H, J=6.2 Hz, H-11α), 5.80 (s, 1H, H-4), 7.25 (d, 2H, J=8.2 Hz, CH-arom.), 7.62 (d, 2H, J=8.4 Hz), 8.31 (s,1H, CH=NOCS).

Example 8

4-[17aβ-Methoxy-17aα-(methoxymethyl)-17a-homo-3-oxooestra-4,9-dien-11β-yl]benzaldehyde (1E)-(O-acetyl)oxime 1 g of 4-[17aβ-methoxy-17aα-(methoxymethyl)-17a-homo-3-oxooestra-4,9-dien-11β-yl]benzaldehyde (1E)-oxime is reacted analogously to Example 4. Crystallization from ethyl acetate gives 0.8 g of 4-[17aβ-methoxy-17aα-(methoxymethyl)-17a-homo-3-oxooestra-4, 9-dien-11β-yl]benzaldehyde (1E)-(O-acetyl)oxime:

$^1$H NMR (400 MHz, CDCl$_3$, δ in ppm with TMS as internal standard): 0.57 (s, 3H, H-18), 2.0 (s, 3H, COCH$_3$), 3.12 and 3.53 (2d, 2H, J=8.6 Hz, CH$_2$O), 3.24, 3.38 (2s, 6H, OCH$_3$), 4.40 (d, 1H, J=6.6 Hz, H-11α), 5.77 (s, 1H, H-4), 7.22 (d, 2H, J=8.4 Hz, CH-arom.), 7.58 (d, 2H, J=8.4 Hz), 7.85 (s, 1H, NOH), 8.33 (s, 1H, CH=N).

The invention claimed is:

1. A 11β-Benzaldoxime compound of formula I:

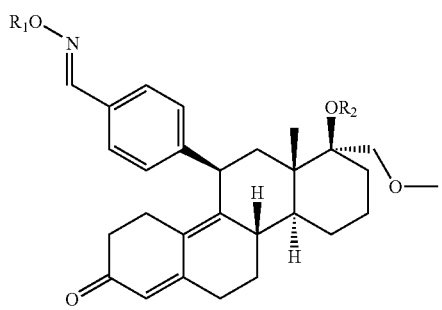

wherein
$R_1$ is a hydrogen atom or a $C_1$-$C_6$-alkyl, $C_1$-$C_6$-acyl, benzoyl, $C_1$-$C_4$-alkoxycarbonyl, $C_1$-$C_4$-alkylthiocarbonyl, $C_1$-$C_6$-alkylaminocarbonyl or arylaminocarbonyl group; and
$R_2$ is a hydrogen atom or a $C_1$-$C_6$-alkyl or $C_1$-$C_6$-acyl group, or pharmaceutically acceptable salts thereof.

2. The compound according to claim 1, wherein
$R_1$ is a hydrogen atom or a $C_1$-$C_4$-alkyl, $C_2$-$C_4$-acyl, $C_1$-$C_4$-alkoxycarbonyl, $C_1$-$C_4$-alkylthiocarbonyl, $C_1$-$C_4$-alkylaminocarbonyl, phenylaminocarbonyl or (4-trifluoromethoxyphenyl)aminocarbonyl group; and
$R_2$ is a hydrogen atom or a methyl, ethyl, acetyl or benzoyl group.

3. The compound according to claim 1, which is
4-[17aβ-hydroxy-17aα-(methoxymethyl)-17a-homo-3-oxooestra-4,9-dien-11β-yl]benzaldehyde (1E)-oxime;
4-[17aβ-hydroxy-17aα-(methoxymethyl)-17a-homo-3-oxooestra-4,9-dien-11β-yl]benzaldehyde (1Z)-oxime;
4-[17aβ-methoxy-17aα-(methoxymethyl)-17a-homo-3-oxooestra-4,9-dien-11β-yl]benzaldehyde (1E)-oxime;
4-[17aβ-acetoxy-17aα-(methoxymethyl)-17a-homo-3-oxooestra-4,9-dien-11β-yl]benzaldehyde (1E)-oxime;
4-[17aβ-hydroxy-17aα-(methoxymethyl)-17a-homo-3-oxooestra-4,9-dien-11β-yl]benzaldehyde (1E)-(O-acetyl)oxime;
4-[17aβ-methoxy-17aα-(methoxymethyl)-17a-homo-3-oxooestra-4,9-dien-11β-yl]benzaldehyde (1E)-(O-acetyl)oxime;
4-[17aβ-hydroxy-17aα-(methoxymethyl)-17a-homo-3-oxooestra-4,9-dien-11β-yl]benzaldehyde (1E)-[O-(methoxy)carbonyl]oxime;
4-[17aβ-methoxy-17aα-(methoxymethyl)-17a-homo-3-oxooestra-4,9-dien-11β-yl]benzaldehyde (1E)-[O-(methoxy)carbonyl]oxime;
4-[17aβ-methoxy-17aα-(methoxymethyl)-17a-homo-3-oxooestra-4,9-dien-11β-yl]benzaldehyde (1E)-[O-(ethoxy)carbonyl]oxime;
4-[17aβ-hydroxy-17aα-(methoxymethyl)-17a-homo-3-oxooestra-4,9-dien-11β-yl]benzaldehyde (1E)-[O-(ethoxy)carbonyl]oxime;
4-[17aβ-methoxy-17aα-(methoxymethyl)-17a-homo-3-oxooestra-4,9-dien-11β-yl]benzaldehyde (1E)-[O-(ethylthio)carbonyl]oxime;
4-[17aβ-methoxy-17aα-(methoxymethyl)-17a-homo-3-oxooestra-4,9-dien-11β-yl]benzaldehyde (1E)-[O-(ethylamino)carbonyl]oxime;
4-[17aβ-hydroxy-17aα-(methoxymethyl)-17a-homo-3-oxooestra-4,9-dien-11β-yl]benzaldehyde (1E)-[O-(ethylamino)carbonyl]oxime; or
4-[17aβ-hydroxy-17aα-(methoxymethyl)-17a-homo-3-oxooestra-4,9-dien-11β-yl]benzaldehyde (1E)-{O-[4'-trifluoromethoxy)phenylamino]-carbonyl}oxime.

4. A process for the preparation of compound according to claim 1 comprising
a) reacting a compound of formula II

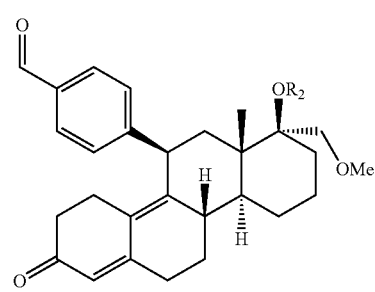

with hydroxylamine in a solvent, in the presence of an organic or inorganic base, to give a compound of formula Ia:

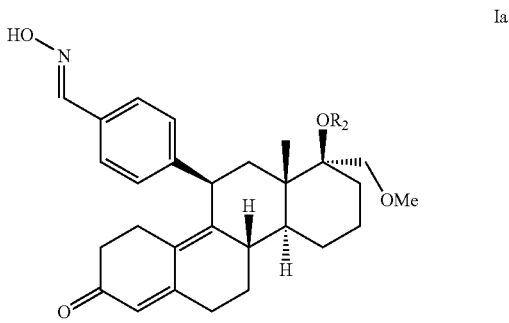

and optionally
b) reacting a compound of formula Ia with a reagent selected from the group consisting of $C_1$-$C_6$-alkyl halides, $C_1$-$C_6$-acyl halides, $C_1$-$C_6$-carboxylic anhydrides, benzoyl halides, $C_1$-C4-alkoxycarbonyl halides, $C_1$-$C_4$-alkythiocarbonyl halides, $C_1$-$C_6$-alkylaminocarbonyl halides, $C_1$-$C_6$-alkyl isocyantes, arylaminocarbonyl halides and aryl isocyanates.

5. A pharmaceutical composition comprising one or more compounds according to claim 1, and pharmacologically acceptable carrier.

6. A method for the treatment of a glucocorticoid-induced androgen deficiency, comprising administering, to a host in need thereof, an effective amount of a compound according to claim 1.

7. A method for the treatment of sexual dysfunction or infertility in men comprising administering, to a host in need thereof, an effective amount of a compound according to claim 1.

* * * * *